(12) United States Patent
Park et al.

(10) Patent No.: US 10,087,276 B2
(45) Date of Patent: Oct. 2, 2018

(54) BLOCK COPOLYMER

(71) Applicant: LG Chem, Ltd., Seoul (KR)

(72) Inventors: No Jin Park, Daejeon (KR); Jung Keun Kim, Daejeon (KR); Je Gwon Lee, Daejeon (KR); Sung Soo Yoon, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/102,156

(22) PCT Filed: Dec. 8, 2014

(86) PCT No.: PCT/KR2014/012031
§ 371 (c)(1),
(2) Date: Jun. 6, 2016

(87) PCT Pub. No.: WO2015/084128
PCT Pub. Date: Jun. 11, 2015

(65) Prior Publication Data
US 2016/0304656 A1 Oct. 20, 2016

(30) Foreign Application Priority Data

| | | | |
|---|---|---|---|
| Dec. 6, 2013 | (KR) | ........................ | 10-2013-0151865 |
| Dec. 6, 2013 | (KR) | ........................ | 10-2013-0151866 |
| Dec. 6, 2013 | (KR) | ........................ | 10-2013-0151867 |
| Dec. 20, 2013 | (KR) | ........................ | 10-2013-0159994 |
| Sep. 30, 2014 | (KR) | ........................ | 10-2014-0131964 |
| Dec. 8, 2014 | (KR) | ........................ | 10-2014-0175411 |

(51) Int. Cl.
| | |
|---|---|
| C08F 293/00 | (2006.01) |
| C08J 7/12 | (2006.01) |
| C07C 43/215 | (2006.01) |
| C07C 43/225 | (2006.01) |
| C07C 217/84 | (2006.01) |
| C07D 209/48 | (2006.01) |
| C08F 12/20 | (2006.01) |
| C08F 12/22 | (2006.01) |
| C08F 12/26 | (2006.01) |
| C08F 12/32 | (2006.01) |
| C07F 7/18 | (2006.01) |
| C08F 212/14 | (2006.01) |
| C08F 220/10 | (2006.01) |
| C08F 220/30 | (2006.01) |
| C08J 5/18 | (2006.01) |
| G03F 7/00 | (2006.01) |
| C07C 35/48 | (2006.01) |
| C08J 7/14 | (2006.01) |
| C09D 153/00 | (2006.01) |
| G03F 7/038 | (2006.01) |
| G03F 7/039 | (2006.01) |
| G03F 7/16 | (2006.01) |
| B81C 1/00 | (2006.01) |
| B82Y 40/00 | (2011.01) |

(52) U.S. Cl.
CPC .......... *C08F 293/005* (2013.01); *C07C 35/48* (2013.01); *C07C 43/215* (2013.01); *C07C 43/225* (2013.01); *C07C 217/84* (2013.01); *C07D 209/48* (2013.01); *C07F 7/1852* (2013.01); *C08F 12/20* (2013.01); *C08F 12/22* (2013.01); *C08F 12/26* (2013.01); *C08F 12/32* (2013.01); *C08F 212/14* (2013.01); *C08F 220/10* (2013.01); *C08F 220/30* (2013.01); *C08J 5/18* (2013.01); *C08J 7/123* (2013.01); *C08J 7/14* (2013.01); *C09D 153/00* (2013.01); *G03F 7/0002* (2013.01); *G03F 7/038* (2013.01); *G03F 7/039* (2013.01); *G03F 7/162* (2013.01); *B81C 1/00428* (2013.01); *B81C 1/00531* (2013.01); *B81C 2201/0149* (2013.01); *B82Y 40/00* (2013.01); *C07C 2601/16* (2017.05); *C08F 2438/03* (2013.01); *C08J 2353/00* (2013.01)

(58) Field of Classification Search
CPC ...... C08F 293/005; C08F 12/20; C08F 12/22; C08F 12/26; C08F 12/32; C08F 212/14; C08F 220/10; C08F 220/30; C08F 2438/03
See application file for complete search history.

(56) References Cited

U.S. PATENT DOCUMENTS

| | | |
|---|---|---|
| 3,976,672 A | 8/1976 | Strunk et al. |
| 5,234,604 A | 8/1993 | Liao et al. |

(Continued)

FOREIGN PATENT DOCUMENTS

| | | |
|---|---|---|
| CN | 1333790 A | 1/2002 |
| CN | 1337974 A | 2/2002 |

(Continued)

OTHER PUBLICATIONS

Tenneti et al. Hierarchical Nanostructures of Mesogen Jacketed Bent-Core Liquid Crystalline Block Copolymers, Proceedings Published 2007 by the American Chemical Society.

(Continued)

*Primary Examiner* — Irina S Zemel
*Assistant Examiner* — Jeffrey S Lenihan
(74) *Attorney, Agent, or Firm* — Lerner, David, Littenberg, Krumholz & Mentlik, LLP

(57) ABSTRACT

The present application provides the block copolymers and their application. The block copolymer has an excellent self assembling property and phase separation and various required functions can be freely applied thereto as necessary.

12 Claims, 2 Drawing Sheets

(56) References Cited

U.S. PATENT DOCUMENTS

| | | |
|---|---|---|
| 5,391,626 A | 2/1995 | Machida et al. |
| 5,418,290 A | 5/1995 | Machida et al. |
| 5,728,431 A | 3/1998 | Bergbreiter et al. |
| 6,531,547 B1 * | 3/2003 | Visger ............... C08F 293/005 508/110 |
| 6,546,282 B1 | 4/2003 | Inoue et al. |
| 6,953,649 B2 | 10/2005 | Prat et al. |
| 7,538,159 B2 | 5/2009 | Wang et al. |
| 8,163,189 B2 | 4/2012 | Iyoda et al. |
| 8,791,042 B2 | 7/2014 | Ronan et al. |
| 9,495,991 B2 | 11/2016 | Han et al. |
| 2003/0143343 A1 | 7/2003 | Kawabata et al. |
| 2004/0049836 A1 | 3/2004 | Ashraf et al. |
| 2004/0110856 A1 | 6/2004 | Young et al. |
| 2004/0143032 A1 | 7/2004 | Auschra et al. |
| 2004/0242787 A1 | 12/2004 | Chun et al. |
| 2006/0166033 A1 | 7/2006 | Poetsch et al. |
| 2007/0142559 A1 | 6/2007 | Wang et al. |
| 2008/0105854 A1 | 5/2008 | Huh et al. |
| 2008/0193658 A1 | 8/2008 | Millward |
| 2008/0286333 A1 | 11/2008 | Kangas et al. |
| 2008/0311402 A1 | 12/2008 | Jung et al. |
| 2009/0114108 A1 | 5/2009 | Oya et al. |
| 2009/0240001 A1 | 9/2009 | Regner |
| 2009/0253867 A1 * | 10/2009 | Takahashi ........... C08F 293/005 525/227 |
| 2009/0306295 A1 | 12/2009 | Mays et al. |
| 2010/0086801 A1 | 4/2010 | Russell et al. |
| 2010/0098876 A1 | 4/2010 | Hanson |
| 2010/0102415 A1 | 4/2010 | Millward et al. |
| 2010/0120985 A1 | 5/2010 | Konishi et al. |
| 2010/0155988 A1 | 6/2010 | Keil et al. |
| 2010/0210742 A1 | 8/2010 | Iyoda et al. |
| 2010/0216312 A1 | 8/2010 | Yamamoto et al. |
| 2010/0266957 A1 | 10/2010 | Harada et al. |
| 2010/0285276 A1 | 11/2010 | Kim et al. |
| 2010/0286351 A1 | 11/2010 | Yoshida et al. |
| 2010/0305230 A1 | 12/2010 | Li et al. |
| 2011/0186544 A1 | 8/2011 | Endou et al. |
| 2011/0253946 A1 | 10/2011 | Huh et al. |
| 2011/0294070 A1 | 12/2011 | Hatakeyama et al. |
| 2012/0052446 A1 | 3/2012 | Jaycox et al. |
| 2012/0116024 A1 | 5/2012 | Iyoda et al. |
| 2012/0214094 A1 | 8/2012 | Mikoshiba et al. |
| 2013/0078576 A1 | 3/2013 | Wu et al. |
| 2013/0183828 A1 | 7/2013 | Nakamura et al. |
| 2013/0189504 A1 | 7/2013 | Nealey et al. |
| 2013/0209693 A1 | 8/2013 | Vogel et al. |
| 2013/0209755 A1 | 8/2013 | Hustad et al. |
| 2013/0248488 A1 | 9/2013 | Han et al. |
| 2013/0284698 A1 | 10/2013 | Ogihara |
| 2013/0306594 A1 | 11/2013 | Hustad et al. |
| 2014/0011916 A1 | 1/2014 | Lee et al. |
| 2014/0127456 A1 | 5/2014 | Regner |
| 2014/0370442 A1 | 12/2014 | Ober et al. |
| 2015/0085042 A1 | 3/2015 | Keoshkerian et al. |
| 2015/0197663 A1 | 7/2015 | Mizutani et al. |
| 2015/0228298 A1 | 8/2015 | Han et al. |
| 2016/0204653 A1 | 7/2016 | Lee |
| 2016/0280831 A1 | 9/2016 | Park et al. |
| 2016/0280832 A1 | 9/2016 | Kim et al. |
| 2016/0280833 A1 | 9/2016 | Lee et al. |
| 2016/0280834 A1 | 9/2016 | Kim et al. |
| 2016/0280835 A1 | 9/2016 | Lee et al. |
| 2016/0304653 A1 | 10/2016 | Kim et al. |
| 2016/0304654 A1 | 10/2016 | Lee et al. |
| 2016/0304655 A1 | 10/2016 | Lee et al. |
| 2016/0311958 A1 | 10/2016 | Kim et al. |
| 2016/0311959 A1 | 10/2016 | Lee et al. |
| 2016/0311960 A1 | 10/2016 | Lee et al. |
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 | 6/1962 |
| JP | 01260360 A | 10/1989 |
| JP | H01-260360 A | 10/1989 |
| JP | H5320281 A | 12/1993 |
| JP | H10237143 A | 9/1998 |
| JP | H1143523 A | 2/1999 |
| JP | 2000053734 A | 2/2000 |
| JP | 2000281737 A | 10/2000 |
| JP | 3121116 B2 | 12/2000 |
| JP | 2001294617 A | 10/2001 |
| JP | 2002-145973 * | 5/2002 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2007070453 A | 3/2007 |
| JP | 2007077292 A | 3/2007 |
| JP | 2009057519 A | 3/2009 |
| JP | 200986354 A | 4/2009 |
| JP | 2009203439 A | 9/2009 |
| JP | 2010115832 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013219334 A | 10/2013 |

(56) References Cited

FOREIGN PATENT DOCUMENTS

| | | | |
|---|---|---|---|
| JP | 2013232501 A | 11/2013 | |
| JP | 2014070154 A | 4/2014 | |
| JP | 2016539239 A | 12/2016 | |
| JP | 2016540863 A | 12/2016 | |
| JP | 2017502116 A | 1/2017 | |
| JP | 2017505356 A | 2/2017 | |
| KR | 20010101356 | 11/2001 | |
| KR | 100622353 B1 | 9/2006 | |
| KR | 20090015742 A | 2/2009 | |
| KR | 100935863 B1 | 1/2010 | |
| KR | 20100033962 A | 3/2010 | |
| KR | 20100070380 A | 6/2010 | |
| KR | 20100123920 A | 11/2010 | |
| KR | 20110018678 A | 2/2011 | |
| KR | 20110086834 A | 8/2011 | |
| KR | 20110097707 A | 8/2011 | |
| KR | 20110102998 A | 9/2011 | |
| KR | 20110112501 A | 10/2011 | |
| KR | 101102680 B1 | 1/2012 | |
| KR | 20120119998 A | 11/2012 | |
| KR | 20130094264 A | 8/2013 | |
| KR | 20130113596 A | 10/2013 | |
| KR | 20130128346 A | 11/2013 | |
| KR | 20140063790 A | 5/2014 | |
| KR | 20150066488 A | 6/2015 | |
| KR | 20150067065 A | 6/2015 | |
| KR | 20150067069 A | 6/2015 | |
| KR | 20150067070 A | 6/2015 | |
| KR | 20160038705 A | 4/2016 | |
| TW | 201323461 A | 6/2013 | |
| TW | 201428046 A | 7/2014 | |
| TW | 201536823 A | 10/2015 | |
| TW | 201538548 A | 10/2015 | |
| WO | 2007055371 A1 | 5/2007 | |
| WO | 2012144735 A2 | 10/2012 | |
| WO | 2013069544 A1 | 5/2013 | |
| WO | 2013120051 A1 | 8/2013 | |
| WO | 2013158527 A1 | 10/2013 | |
| WO | WO-2014050905 A1 * | 4/2014 | |
| WO | 2014090178 A1 | 6/2014 | |
| WO | 2014124795 A1 | 8/2014 | |
| WO | 2015084121 A1 | 6/2015 | |
| WO | 2015084122 A1 | 6/2015 | |
| WO | 2015084123 A1 | 6/2015 | |
| WO | 2015084124 A1 | 6/2015 | |
| WO | 2015084125 A1 | 6/2015 | |
| WO | 2015084126 A1 | 6/2015 | |
| WO | 2015084127 A1 | 6/2015 | |
| WO | 2015087005 A1 | 6/2015 | |
| WO | 2016052994 A1 | 4/2016 | |
| WO | 2016052999 A1 | 4/2016 | |
| WO | 2016053005 A1 | 4/2016 | |
| WO | 2016053007 A1 | 4/2016 | |

OTHER PUBLICATIONS

Tenneti et al. "Competition between liquid crystallinity and block copolymer self-assembly in core-shell rod-coil block copolymers", Soft Matter, 2008, 4, 458-461 (2008).
Hua et al. Temperature-induced phase-transitions of methoxyoligo(oxyethylene) styrene-based block copolymers in aqueous solution, Soft Matter, published Aug. 2013, 9, 8897.
Khazimullis et al. "Gel formation in a mixture of a block copolymer and a nematic liquid crystal", Physical Review E 84, 021710 (2011).
International Search Report from PCT/KR2014/012023, dated Mar. 10, 2015.
IPO Search Report from Taiwan Application No. 103142955, dated Jan. 15, 2016.
International Search Report from PCT/KR2014/012024, dated Mar. 17, 2015.
IPO Search Report from Taiwan Application No. 103142805, dated Dec. 11, 2015.
International Search Report from PCT/KR2014/012025, dated Mar. 17, 2015.
IPO Search Report from Taiwan Application No. 103142784, dated Jan. 27, 2016.
International Search Report from PCT/KR2014/012026, dated Mar. 17, 2015.
International Search Report from PCT/KR2014/012027, dated Mar. 17, 2015.
IPO Search Report from Tawain Application No. 103142782, dated Dec. 11, 2015.
International Search Report from PCT/KR2014/012028, dated Mar. 17, 2015.
IPO Search Report from Taiwan Application No. 103142798, dated Dec. 16, 2015.
International Search Report from PCT/KR2014/012029, dated Mar. 17, 2015.
IPO Search Report from Taiwan Application No. 103142780, dated Dec. 15, 2015.
International Search Report from PCT/KR2014/012030, dated Mar. 17, 2015.
IPO Search Report from Taiwan Application No. 103142790, dated Dec. 15, 2015.
International Search Report from PCT/KR2014/012031, dated Feb. 12, 2015.
IPO Search Report from Taiwan Application No. 103142956 dated Jan. 20, 2016.
International Search Report from PCT/KR2014/012032, dated Feb. 12, 2015.
IPO Search Report from Taiwan Application No. 103142777, dated Dec. 15, 2015.
International Search Report from PCT/KR2014/012033, dated Feb. 12, 2015.
IPO Search Report from Taiwan Application No. 103142963, dated Dec. 10, 2015.
International Search Report from PCT/KR2014/012034, dated Feb. 12, 2015.
IPO Search Report from Taiwan Application No. 103142745, dated Dec. 14, 2015.
International Search Report from PCT/KR2014/012035, dated Feb. 12, 2015.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
IPO Search Report from Taiwan Application No. 103142794, dated Dec. 15, 2015.
IPO Search Report from Taiwan Application No. 103142786, dated Jan. 11, 2016.
International Search Report from PCT/KR2014/012036, dated Mar. 17, 2015.
International Search Report from PCT/KR2015/10338 dated Jan. 14, 2016.
International Search Report from PCT/KR2015/010313, dated Nov. 23, 2015.
International Search Report from PCT/KR2015/010335 dated Jan. 13, 2016.
IPO Search Report from Taiwan Application No. 104132186, dated Aug. 18, 2016.
International Search Report from PCT/KR2015/010334, dated Jan. 13, 2016.
International Search Report from PCT/KR2015/010323, dated Jan. 13, 2016.
International Search Report from PCT/KR2015/010320, dated Jan. 13, 2016.
International Search Report from PCT/KR2015/010322, dated Jan. 13, 2016.
International Search Report from PCT/KR2015/010327, dated Jan. 12, 2016.
International Search Report from PCT/KR2015/010330 dated Jan. 11, 2016.
Park et al., "Block Copolymer Lithography: Periodic Arrays of ~10 11 Holes in 1 Square Centimeter", Science 276, p. 1401-1404, May 30, 1997.

(56) References Cited

OTHER PUBLICATIONS

International Search Report from PCT/KR2015/010332 dated Jan. 13, 2016.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
Choi et al., U.S. Appl. No. 15/514,939, filed Mar. 28, 2017, titled "Block Copolymer".
Kim et al., U.S. Appl. No. 15/101,794, filed Jun. 3, 2016, titled "Monomer and Block Copolymer".
Kim et al., U.S. Appl. No. 15/102,089, filed Jun. 6, 2016, titled "Block Copolymer".
Kim et al., U.S. Appl. No. 15/173,671, filed Jun. 5, 2016, titled "Block Copolymer".
Kim et al., U.S. Appl. No. 15/173,674, filed Jun. 5, 2016, titled "Block Copolymer".
Kim et al., U.S. Appl. No. 15/515,818, filed Mar. 30, 2017, titled "Block Copolymer".
Ku et al., U.S. Appl. No. 15/514,929, filed Mar. 28, 2017, titled "Method of Manufacturing Patterned Substrate".
Ku et al., U.S. Appl. No. 15/515,432, filed Mar. 29, 2017, titled "Method of Manufacturing Patterned Substrate".
Lee et al., U.S. Appl. No. 15/101,812, filed Jun. 3, 2016, titled "Block Copolymer".
Lee et al., U.S. Appl. No. 15/101,827, filed Jun. 3, 2016, titled "Block Copolymer".
Lee et al., U.S. Appl. No. 15/101,915, filed Jun. 5, 2016, titled "Block Copolymer".
Lee et al., U.S. Appl. No. 15/102,112, filed Jun. 6, 2016, titled "Block Copolymer".
Lee et al., U.S. Appl. No. 15/102,139, filed Jun. 6, 2016, titled "Block Copolymer".
Lee et al., U.S. Appl. No. 15/102,149, filed Jun. 6, 2016, titled "Block Copolymer".
Lee et al., U.S. Appl. No. 15/173,673, filed Jun. 5, 2016, titled "Block Copolymer".
Lee et al., U.S. Appl. No. 15/173,676, filed Jun. 5, 2016, titled "Block Copolymer".
Lee et al., U.S. Appl. No. 15/514,959, filed Mar. 28, 2017, titled "Block Copolymer".
Lee et al., U.S. Appl. No. 15/514,967, filed Mar. 28, 2017, titled "Block Copolymer".
Lee et al., U.S. Appl. No. 15/515,293, filed Mar. 29, 2017, titled "Block Copolymer".
Lee et al., U.S. Appl. No. 15/515,812, filed Mar. 30, 2017, titled "Block Copolymer".
Lee et al., U.S. Appl. No. 15/515,821, filed Mar. 30, 2017, titled "Block Copolymer".
Park et al., U.S. Appl. No. 15/173,670, filed Jun. 5, 2016, titled "Block Copolymer".
Park et al., U.S. Appl. No. 15/515,290, filed Mar. 29, 2017, titled "Block Copolymer".
CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: "Fluorescence Anisotropy of Hydrophobic Probes in poly(N-decylacrylamide) block-poly( N,N-diethylacrylamide) Block Copolymer Aqueous Solutions: Evidence of Premicellar Aggregates" Journal of Physical Chemistry Part B: Condensed Matter, Materials, Surfaces, Interfaces & BiOphysical, vol. 114, No. 31, Aug. 12, 2010 (Aug. 12, 2010), 9977-9986, XP055394763, US ISSN: 1520-6106, DOI: 10.1021/jp101613y * abstract ** Scheme 1, PDcA11-block-PDEA295; p. 9978 *.
Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998] * abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 DOI: 10.1002/macp.200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate)" Macromolecules American Chemical Society US vol. 27 No. 15 Jul. 18, 1994 (Jul. 18, 1994) pp. 4093-4100 XP000456650 ISSN: 0024-9297 DOI: 10.1021/MA00093A010 * abstract *.
Anonymous., "Solid surface energy data (SFE) for common polymers", surface-tension.de, Feb. 2017, Retrieved from the Internet: URL:http://www.surface-tension.de/solid-surface-energy.htm, XP002775246.
Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
Chinese Search Report for Application No. 201480072759.9 dated Jan. 24, 2018.
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
Chinese Search Report for CN Application No. 201480071920.0, dated May 4, 2018.
Chinese Search Report for CN Application No. 201480072800.2, dated Apr. 10, 2018.
Chinese Search Report for CN Application No. 201480074045.1, dated Apr. 11, 2018.
Extended European Seach Report including Written Opinion for EP Application No. 15847574.9, dated May 3, 2018.

(56) References Cited

OTHER PUBLICATIONS

Extended European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.
Extended European Search Report with Written Opinion for EP158468322 dated May 3, 2018.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp.200700312.
Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.
Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.
Palacios et al., Constructing Robust and Functional Micropatterns on Polystyrene Surfaces by Using Deep UV Irradiation, American Chemical Society, Langmuir, 29(8) pp. 2756-2763, Feb. 2013.
Segalman R.A. et al., "Graphoepitaxy of Spherical Domain Block Copolymer Films," Advanced Materials, Wiley-VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.
Supplementary European Search Report for EP15847157 dated Mar. 21, 2018.

* cited by examiner

BLOCK COPOLYMER

CROSS-REFERENCE TO RELATED APPLICATION

This application is a national phase entry under 35 U.S.C. § 371 of International Application No. PCT/KR2014/012031, filed Dec. 8, 2014, which claims priority to Korean Patent Application No. 10-2013-0151866, filed Dec. 6, 2013, Korean Patent Application No. 10-2013-0151865, filed Dec. 6, 2013, Korean Patent Application No. 10-2013-0151867, filed Dec. 6, 2013, Korean Patent Application No. 10-2013-0159994, filed Dec. 20, 2013, Korean Patent Application No. 10-2014-0131964, filed Sep. 30, 2014 and Korean Patent Application No. 10-2014-0175411, filed Dec. 8, 2014, the disclosures of which are incorporated herein by reference.

TECHNICAL FIELD

The present application relates to a block copolymer.

BACKGROUND

Block copolymers have molecular structures in which polymer subunits having chemically different structures from each other are linked by covalent bonds. Block copolymers are capable of forming periodically aligned structure such as the sphere, the cylinder or the lamella through phase separations. Sizes of domains of the structures formed by the self assemblies of block copolymers may be adjusted in a wide range, and various shapes of structures can be prepared. Therefore, they can be utilized in pattern-forming methods by lithography, various magnetic recording mediae or next generation nano devices such as metal dots, quantum dots or nano lines, high density magnetic storage mediae, and the like.

DESCRIPTION

Technical Object

The present application provides a block copolymer and its application.

Technical Solution

Figure 1:
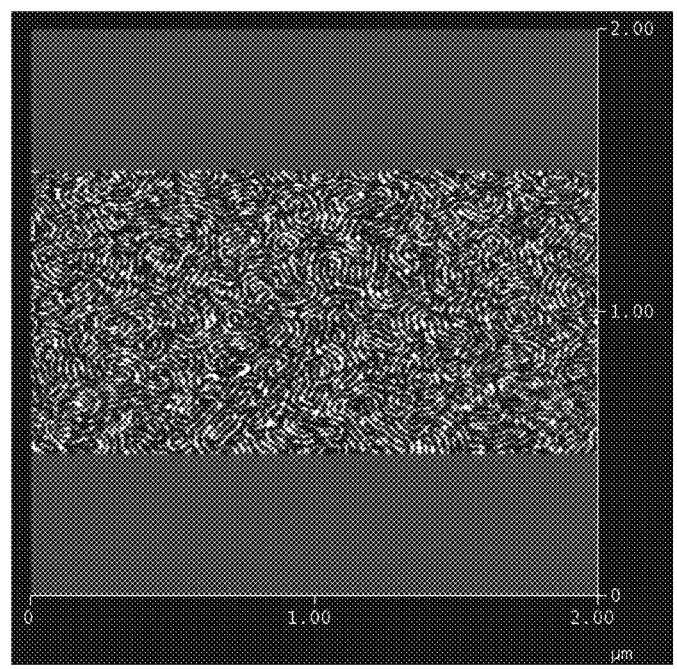
FIG. 1 shows an observation by the AFM (atomic force microscope) of nano structures of a polymer layer comprising a self assembled product of the block copolymer of Example 1.

The term "alkyl group" as used herein may refer to, unless defined otherwise, an alkyl group having 1 to 20, 1 to 16, 1 to 12, 1 to 8, or 1 to 4 carbon atoms. The alkyl group may have a linear, branched or cyclic structure, and may be optionally substituted with at least one substituent.

The term "alkoxy group" as used herein may refer to, unless defined otherwise, an alkoxy group having 1 to 20, 1 to 16, 1 to 12, 1 to 8, or 1 to 4 carbon atoms. The alkoxy group may have a linear, branched, or cyclic structure, and may be optionally substituted with at least one substituent.

The term "alkenyl or alkynyl group" as used herein may refer to, unless defined otherwise, an alkenyl or alkynyl group having 2 to 20, 2 to 16, 2 to 12, 2 to 8, or 2 to 4 carbon atoms. The alkenyl or alkynyl group may have a linear, branched, or cyclic structure, and may be optionally substituted with at least one substituent.

The term "alkylene group" as used herein may refer to, unless defined otherwise, an alkylene group having 1 to 20, 1 to 16, 1 to 12, 1 to 8 or 1 to 4 carbon atoms. The alkylene group may have a linear, branched, or cyclic structure, and may be optionally substituted with at least one substituent.

The term "alkenylene or alkynylene group" as used herein may refer to, unless defined otherwise, an alkenylene or alkynylene group having 2 to 20, 2 to 16, 2 to 12, 2 to 8 or 2 to 4 carbon atoms. The alkenylene or alkynylene group may have a linear, branched, or cyclic structure, and may be optionally substituted with at least one substituent.

The term "aryl or arylene group" as used herein may be, unless defined otherwise, a monovalent or bivalent substituent derived from a compound including one benzene ring structure or a structure, in which at least two benzene rings are linked with sharing one or two carbon atoms or by an optional linker, or a derivative of the compound. The aryl or arylene group may be, unless defined otherwise, an aryl group having 6 to 30, 6 to 25, 6 to 21, 6 to 18, or 6 to 13 carbon atoms.

The term "aromatic structure" as used herein may refer to the aryl group or the arylene group.

The term "alicyclic structure" as used herein may refer to, unless defined otherwise, a cyclic hydrocarbon structure that is not the aromatic cyclic structure. The alicyclic structure may be, unless defined otherwise, a structure having 3 to 30, 3 to 25, 3 to 21, 3 to 18 or 3 to 13 carbon atoms.

The term "single bond" as used herein may refer to a case where there is no atom in a corresponding site. For example, a case where "B" is a single bond in the structure represented by "A-B-C," means that there is no atom in the "B" position and therefore the structure represented by "A-C" is formed by the "A" directly connecting to the "C."

A substituent that may optionally substitute for the alkyl group, the alkenyl group, the alkynyl group, the alkylene group, the alkenylene group, the alkynylene group, the alkoxy group, the aryl group, the arylene group, a chain, the aromatic structure, and the like may be hydroxyl group, halogen atom, carboxyl group, glycidyl group, acryloyl group, methacryloyl group, acryloyloxy group, methacryloyloxy group, thiol group, alkyl group, alkenyl group, alkynyl group, alkylene group, alkenylene group, alkynylene group, alkoxy group or aryl group, but is not limited thereto.

Illustrative block copolymer of the present application may include a block represented by Formula 1 below:

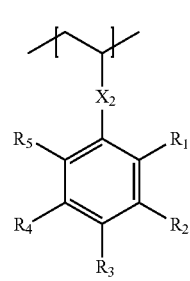

[Formula 1]

In Formula 1, the $X_2$ may be a single bond, an oxygen atom, a sulfur atom, $-S(=O)_2-$, an alkylene group, an alkenylene group, an alkynylene group, the $R_1$ to $R_5$ may be each independently hydrogen, an alkyl group having 1 to 8 carbon atoms or a linear chain having 9 or more chain-forming atoms and at least one of the $R_1$ to $R_5$ may be the linear chain having 9 or more chain-forming atoms.

In one embodiment, the $X_2$ of Formula 1 may be the single bond or the oxygen atom; or may be the single bond, but is not limited thereto.

In the Formula 1, the $R_1$ to $R_5$ may be each independently hydrogen, an alkyl group having 1 to 8 carbon atom(s) or the linear chain comprising 9 or more chain-forming atoms. At least one of the $R_1$ to $R_5$ may be the linear chain comprising 9 or more chain-forming atoms.

In one embodiment, among the $R_1$ to $R_5$, the $R_1$, $R_2$, $R_4$ and $R_5$ may be each independently hydrogen or an alkyl group having 1 to 8 carbon atom(s); or may be each independently hydrogen or an alkyl group having 1 to 4 carbon atom(s); or may be hydrogen; and the $R_3$ may be the linear chain having 9 or more chain-forming atoms.

The term "chain-forming atoms" as used herein refers to atoms forming a linear structure of a certain chain. The chain may have a linear or branched structure; however the number of the chain-forming atoms is calculated only by the number of atoms forming the longest linear chain. Therefore, other atoms such as, in a case where the chain-forming atom is the carbon atom, the hydrogen atom that is linked to the carbon atom and the like are not calculated as the number of the chain-forming atoms. Further, in case of the branched chain, the number of the chain-forming atoms is the number of atoms forming the longest chain. For example, the chain is n-pentyl, all of the chain-forming atoms are carbon atoms and the number thereof is 5. If the chain is 2-methylpentyl, all of the chain-forming atoms are also carbon atoms and the number thereof is 5. The chain-forming atoms may be the carbon, the oxygen, the sulfur or the nitrogen, and the like and appropriate chain-forming atoms may be the carbon, the oxygen or the nitrogen; or the carbon or the oxygen. The number of the chain-forming atoms may be 8 or more, 9 or more, 10 or more, 11 or more; or 12 or more. The number of the chain-forming atoms may be 30 or less, 25 or less, 20 or less or 16 or less.

The unit of the Formula 1 makes it possible for the block copolymer to exhibit an excellent self assembling property.

In one embodiment, the chain may be a linear hydrocarbon atom such as a linear alkyl group. In this case, the alkyl group may be an alkyl group comprising 9 or more, 9 to 30, 9 to 25, 9 to 20 or 9 to 16 carbon atoms. At least one carbon atom among carbon atoms of the alkyl group may be optionally replaced with an oxygen atom; and at least one hydrogen atom of the alkyl group may be optionally substituted with another substituent.

Optionally, the linear hydrocarbon chain may include at least one heteroatom. The heteroatom may be an oxygen atom or a nitrogen atom.

The chain may be, for example, an alkyl group, an alkoxy group or an alkoxyalkyl group. In this case, the number of the carbon atom(s) and the oxygen atom(s) in the alkyl group, the alkoxy group or the alkoxyalkyl group may be 9 or more, 9 to 30, 9 to 25, 9 to 20 or 9 to 16.

Another block (hereinafter, may be referred to as a "second block") that may be included in the block copolymer along with the first block is not particularly limited.

For example, the second block may be polyvinylpyrrolidone block, polylactic acid block, polyvinylpyridine block, polystyrene block such as polystyrene block or polytrimethylsilylstyrene, polyalkyleneoxide block such as polyethyleneoxide block, polyacrylate block, or polyolefin block such as polyethylene block or polyisoprene block or polybutadiene block.

In one embodiment, the second block may be represented by Formula 2 below.

The block copolymer may further comprise the second block may be represented by Formula 2 below.

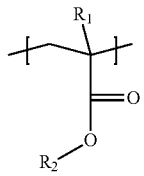

[Formula 2]

In the Formula 2, the $R_1$ may be hydrogen or an alkyl group and the $R_2$ may be an alkyl group.

In one embodiment, the $R_1$ of the Formula 2 may be hydrogen or an alkyl group having 1 to 4 carbon atom(s); or may be hydrogen or methyl group; or may be a methyl group.

In one embodiment, the $R_2$ of the Formula 2 may be an alkyl group comprising 1 to 20, 1 to 16, 1 to 12, 1 to 8 or 1 to 4 carbon atom(s).

A specific method for preparing the block copolymer is not particularly limited, as long as it comprises a step forming at least one block of the block copolymer by using monomers capable of forming the blocks.

For example, the block copolymer may be prepared by a living radical polymerization (LRP) using the monomer. For example, there are methods such as the anionic polymerization, in which block copolymers are synthesized in the presence of inorganic acid salts such as salts of alkali metal or alkali earth metal by using organic rare earth metal complexes or organic alkali metal compounds as polymerization initiators; the anionic polymerization, in which block copolymers are synthesized in the presence of organic aluminum compounds by using organic alkali metal compounds as polymerization initiators; the atom-transfer radical polymerization (ATRP) using an atom transfer radical polymerizer as a polymerization controller; the activators regenerated by electron transfer (ATGET) ATRP performing polymerization in the presence of an organic or inorganic reducing agent generating electrons using an atom transfer radical polymerizer as a polymerization controller; the initiators for continuous activator regeneration (ICAR) ATRP; the reversible addition-ring opening chain transfer (RAFT) polymerization using an inorganic reducing agent reversible addition-ring opening chain transfer agent; and the a method using an organic tellurium compound as an initiator, and an appropriate method may be selected among the above methods.

In one embodiment, the block copolymer may be prepared by a method including polymerizing a material comprising monomers capable of forming the block in the presence of radical initiators and living radical polymerization reagents by the living radical polymerization.

In the preparation of the block copolymer, a method for forming other block included in the block copolymer along with the block formed by the above monomer is not particularly limited, and the other block may be formed by selecting appropriate monomers considering the kind of blocks to be formed.

The method for preparing the block copolymer may further include precipitating a polymerized product produced by the above-described process in a non-solvent.

A kind of the radical initiators may be suitably selected in consideration of polymerization efficiency without particular limitation, and an azo compound such as azobisisobutyronitrile (AIBN) or 2,2'-azobis-(2,4-dimethylvaleronitrile), or a peroxide compound such as benzoyl peroxide (BPO) or di-t-butyl peroxide (DTBP) may be used.

The LRP may be performed in a solvent such as methylenechloride, 1,2-dichloroethane, chlorobenzene, dichlorobenzene, benzene, toluene, acetone, chloroform, tetrahydrofuran, dioxane, monoglyme, diglyme, dimethylformamide, dimethylsulfoxide or dimethylacetamide.

As the non-solvent, for example, an alcohol such as methanol, ethanol, normal propanol or isopropanol, a glycol such as ethyleneglycol, or an ether compound such as n-hexane, cyclohexane, n-heptane or petroleum ether may be used without limitation.

Block copolymers may be phase-separated, since they comprise two or more polymer chains linked to each other via covalent bonds. The block copolymer of the present application shows excellent phase separation properties, if necessary, may form nano scaled structure by a microphase separation. The shape or size of the nano scaled structure may be controlled by the size (the molecular weight and the like) of the block copolymer or relative ratios of blocks. The structure formed by the phase separation may include the sphere, the cylinder, the gyroid, the lamella and the reversed structure, and the ability forming the above structure may be referred to as a self assembling properties.

The block copolymer may have, for example, a number average molecular weight (Mn) in a range from approximately 3,000 to 300,000. The term "number average molecular weight" as used herein may refer to a converted value with respect to the standard polystyrene measured by the GPC (Gel Permeation Chromatography). Unless defined otherwise, the term "molecular weight" as used herein may refer to the number average molecular weight. The molecular weight (Mn), in another embodiment, may be, for example, 3000 or more, 5000 or more, 7000 or more, 9000 or more, 11000 or more, 13000 or more or 15000 or more. The molecular weight (Mn), in another embodiment, may be, for example, 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. The block copolymer may have the polydispersity (Mw/Mn) in a range from 1.01 to 1.60. In another embodiment, the polydispersity may be about 1.1 or more, about 1.2 or more, about 1.3 or more, or about 1.4 or more.

In the above range, the block copolymer may exhibit an appropriate self assembling property. The number average molecular weight and the like of the block copolymer may be controlled considering the objected self assembled structure.

If the block copolymer at least includes the first and second blocks, a ratio of the first block, for example, the block including the chain in the block copolymer may be in a range of 10 mole % to 90 mole %.

The present application relates to a polymer layer including the block copolymer. The polymer layer may be used in various applications. For example, it can be used in a biosensor, a recording media such as a flash memory, a magnetic storage media or the pattern forming method or an electric device or an electronic device, and the like.

In one embodiment, the block copolymer in the polymer layer may be forming a periodic structure including a sphere, a cylinder, a gyroid, or a lamella by the self assembly.

For example, in one segment of the first block or the second block or other block linked to the above block via a covalent bond in the block copolymer, other segment may be forming the regular structure such as lamella form, cylinder form and the like.

The present application relates also to a method for forming a polymer layer by using the block copolymer. The method may include forming a polymer layer including the block copolymer on a substrate in a self-assembled state. For example, the method may include forming a layer of the block copolymer or a coating solution in which the block copolymer is diluted in suitable solvent on the substrate by a coating and the like, and if necessary, then aging or heat-treating the layer.

The aging or the heat treatment may be performed based on, for example, a phase transition temperature or glass transition temperature of the block copolymer, and for example, may be performed at a temperature higher than the glass transition temperature or phase transition temperature. A time for the heat treatment is not particularly limited, and the heat treatment may be performed for approximately 1 minute to 72 hours, but may be changed if necessary. In addition, the temperature of the heat treatment of the polymer layer may be, for example, 100° C. to 250° C., but may be changed in consideration of the block copolymer used herein.

The formed layer may be aged in a non-polar solvent and/or a polar solvent at the room temperature for approximately 1 minute to 72 hours.

The present application relates also to a pattern-forming method. The method may include selectively removing the first or second block of the block copolymer from a laminate comprising a substrate and a polymer layer that is formed on a surface of the substrate and that includes a self-assembled block copolymer. The method may be a method for forming a pattern on the above substrate. For example, the method may include forming the polymer layer on the substrate, selectively removing one block or two or more blocks of the block copolymer that is in the polymer layer; and then etching the substrate. By the above method, for example, nano-scaled micropattern may be formed. Further, according to shapes of the block copolymer in the polymer layer, various shapes of pattern such as nano-rod or nano-hole can be formed by the above method. If necessary, in order to form a pattern, the block copolymer may be mixed with another copolymer or homopolymer. A kind of the substrate applied to this method may be selected without particular limitation, and, for example, silicon oxide and the like may be applied.

For example, according to the method, a nano-scale pattern of silicon oxide having a high aspect ratio may be formed. For example, various types of patterns such as a nanorod or nanohole pattern may be formed by forming the polymer layer on the silicon oxide, selectively removing any one block of the block copolymer in a state where the block copolymer in the polymer layer is formed in a predetermined structure, and etching the silicon oxide in various methods, for example, reactive ion etching. In addition, according to the above method, a nano pattern having a high aspect ratio can be formed.

For example, the pattern may be formed to a scale of several tens of nanometers, and such a pattern may be applied in various uses including a next-generation information electronic magnetic recording medium.

For example, a pattern in which nano structures, for example, nanowires, having a width of approximately 3 to 40 nm are disposed at an interval of approximately 6 to 80 nm may be formed by the above-described method. In another embodiment, a structure in which nanoholes having a width, for example, a diameter of approximately 3 to 40 nm are disposed at an interval of approximately 6 to 80 nm can be implemented.

In addition, in this structure, nanowires or nanoholes may be formed to have a high aspect ratio.

In this method, a method of selectively removing any one block of the block copolymer is not particularly limited, and for example, a method of removing a relatively soft block by irradiating a suitable electromagnetic wave, for example, ultra violet rays to a polymer layer may be used. In this case, conditions for ultra violet radiation may be determined according to a type of the block of the block copolymer, and ultra violet rays having a wavelength of approximately 254 nm may be irradiated for 1 to 60 minutes.

In addition, followed by the ultra violet radiation, the polymer layer may be treated with an acid to further remove a segment degraded by the ultra violet rays.

In addition, the etching of the substrate using the polymer layer from which a block is selectively removed may be performed by reactive ion etching using $CF_4$/Ar ions, and followed by the above process, and removing the polymer layer from the substrate by oxygen plasma treatment may be further performed.

Effects

The present application may provide the block copolymers and their application. The block copolymer has an excellent self assembling property and phase separation and various required functions can be freely imparted thereto as necessary.

ILLUSTRATIVE EMBODIMENTS

Hereinafter, the present application will be described in detail with reference to Examples and Comparative Examples, but the scope of the present application is not limited to the following examples.

1. NMR Analysis

The NMR analysis was performed at the room temperature by using a NMR spectrometer including a Varian Unity Inova (500 MHz) spectrometer having a triple resonance 5 mm probe. A sample to be analyzed was used after diluting it in solvent ($CDCl_3$) for the NMR analysis to a concentration of approximately 10 mg/ml and a chemical shift ($\delta$) was expressed in ppm.

Abbreviation br=wide signal, s=singlet, d=doublet, dd=double doublet, t=triplet, dt=double triplet, q=quadruplet, p=quintuplet, m=multiplet 2. GPC (Gel Permeation Chromatograph)

The number average molecular weight and the polydispersity were measured by the GPC (Gel Permeation Chromatograph) and the measuring conditions are as below.

<GPC Measuring Condition>
Device: a 1200 series from Agilent technologies, Co.
Column: two of PLgel mixed B from Polymer laboratories, Co. were used
Solvent: THF
Temperature of the column: 35° C.
Concentration of Sample: 1 mg/mL, 200 L injection
Standard Sample: Polystyrene (Mp: 3900000, 723000, 316500, 52200, 31400, 7200, 3940, 485)

In a 5 mL vial, a block copolymer or a macroinitiator to be measured of Example or Comparative Example and then diluted to a concentration of about 1 mg/mL. Then, the standard sample for a calibration and a sample to be analyzed were filtered by a syringe filter (pore size: 0.45 μm) and then analyzed. ChemStation from the Agilent technologies, Co. was used as an analysis program. The number average molecular weight (Mn) and the weight average molecular weight (Mw) were obtained by comparing an elution time of the sample with a calibration curve and then the polydispersity (PDI) was obtained from their ratio (Mw/Mn).

Preparation Example 1. Synthesis of Para-Dodecyl Styrene (A)

The p-dodecyl styrene was synthesized as below. A Grignard reagent was prepared by putting 4-bromostyrene (5.0 g, 27.3 mmole) and Mg turnings (0.664 g, 27.31 mmole) in a 100 mL flask; dissolving them in 30 mL of tetrahydrofuran from which water was removed; adding a small amount of iodine as a catalyst; and then reacting them by stirring for about 6 hours at the room temperature under a nitrogen. 1-bromododecane was put into another 100 mL flask, and then the Grignard reagent synthesized above was slowly added at 0° C. Then, dilithium tetrachlorocuprate (II) solution (8.2 mL, 0.92 mmole) was added thereto, the flask was heated to the room temperature and the mixture was reacted by stirring for 3 hours. After the reaction, the tetrahydrofuran was removed, and the objected compound was purified in a column chromatography using hexane as a mobile phase and thereby transparent liquid objected compound (2.54 g, 9.32 mmole) was obtained.

<NMR Analysis Result>
$^1$H-NMR($CDCl_3$): $\delta$7.33 (dd, 2H); $\delta$7.14 (dd, 2H); $\delta$6.70 (dd, 1H); $\delta$5.71 (d, 1H); $\delta$5.18 (d, 1H); $\delta$2.59 (t, 2H); $\delta$1.60 (p, 2H); $\delta$1.31-1.26 (m, 18H); $\delta$0.89 (t, 3H)

Preparation Example 2. Synthesis of Para-Dodecyloxymethyl Styrene (B)

The p-dodecyloxymethyl styrene (B) was synthesized as below. In a 500 mL flask, 4-chloromethylstyrene (22.1 g, 144.8 mmole) and 1-dodecanol (30.0 g, 160.1 mmole) was dissolved in 300 mL of tetrahydrofuran and then cooled to 0° C. Sodium hydride (NaH) (7.7 g, 320.8 mmole) was added thereto; and the mixture was reacted by stirring for an hour; was heated to 70° C. and then was reacted for 24 hours. After the reaction, the reacted product was cooled to the room temperature and the remaining sodium hydride was removed by reacting it with small amounts of water in iced water and then removing solids by filtering. Tetrahydrofuran that was a reaction solvent was removed; an organic layer was collected by a fractional extraction using a dichloromethane/secondary purified water and then transparent liquid objected compound (23.9 g, 79.0 mmole) was obtained by a column chromatography using hexane/dichloromethane as a mobile phase.

<NMR Analysis Result>
$^1$H-NMR($CDCl_3$): $\delta$7.39 (dd, 2H); $\delta$7.30 (dd, 2H); $\delta$ 6.71 (dd, 1H); $\delta$5.74 (d, 1H); $\delta$5.23 (d, 1H); $\delta$4.49 (s, 2H); $\delta$3.46 (t, 2H); $\delta$1.61 (p, 2H); $\delta$1.37-1.26 (m, 16H); $\delta$0.89 (t, 3H)

Example 1

A macroinitiator (a number average molecular weight (Mn): 7000, a polydispersity (PDI): 1.16) was synthesized by reacting methyl methacrylates with RAFT (reversible addition-fragmentation chain transfer agent) reagent and AIBN (azobisisobutyronitrile) as a thermal initiator. The synthesized macroinitiator, the compound (A) prepared in the preparation example 1 and azobisisobutyronitrile (AIBN) was dissolved in toluene in a weight ratio 1:70:0.5 (the macroinitiator:the compound (A):AIBN) (the solvent: 20 weight %), and then reacted under a nitrogen for 16 hours at 80° C. and thereby a block copolymer was prepared. The number average molecular weight of the block copolymer was 19200 and the polydispersity was 1.17.

Example 2

The macroinitiator (a number average molecular weight (Mn): 8400, a polydispersity (PDI): 1.15) was synthesized by the same method as described in Example 1 and then a block copolymer was prepared by the same method as described in Example 1, except that the compound (B) in the preparation example 2 was used instead of the compound (A) in the preparation example 1. The number average molecular weight of the block copolymer was 21900 and the polydispersity was 1.19.

Test Example 1

Figure 2:
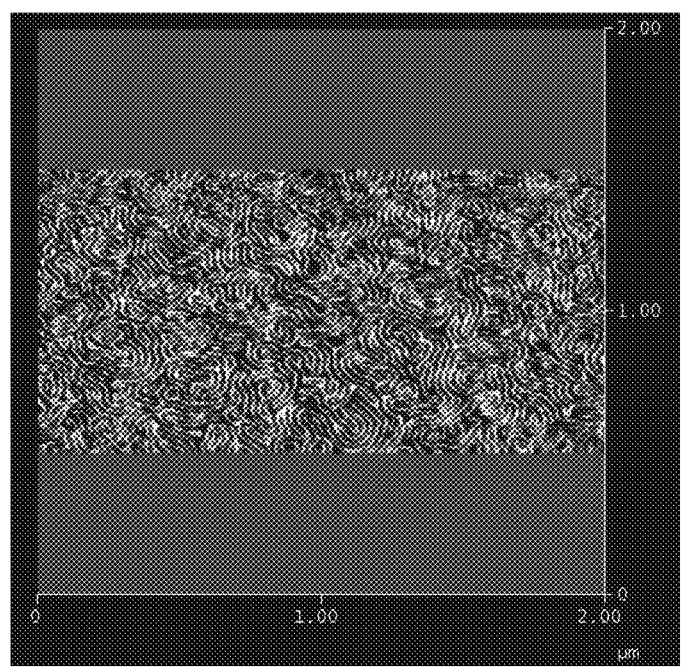
FIG. 2 shows an observation by the AFM (atomic force microscope) of nano structures of a polymer layer comprising a self assembled product of the block copolymer of Example 2.

A polymer layer was formed by coating a coating solution prepared by dissolving the block copolymer of Example 1 or 2 in toluene in a concentration of about 1.0 weight % on a silicone wafer substrate by using a spin coater at a speed of 3000 rpm for 60 seconds. The polymer layer was subjected to a heat treatment at 160° C. for an hour and thereby nano structures were realized in the surface thereof. The realized nano structures were observed by the AFM (atomic force microscope). FIG. 1 is the result of the Example 1 and FIG. 2 is the result of the Example 2.

What is claimed is:

1. A block copolymer comprising a first block and a second block, wherein the block copolymer is a diblock copolymer, the first block is represented by Formula 1 below, and the second block consists of a polyacrylate block represented by Formula 2 below:

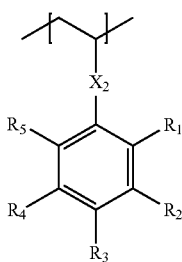

[Formula 1]

wherein the $X_2$ is a single bond, an oxygen atom, a sulfur atom, $S(=O)_2$, an alkylene group, an alkenylene group, an alkynylene group, the $R_1$ to $R_5$ are each independently hydrogen, an alkyl group having 1 to 8 carbon atoms or a linear chain having 9 or more chain-forming atoms and at least one of the $R_1$ to $R_5$ is the linear chain having 9 or more chain-forming atoms, wherein the chain-forming atoms comprise at least one hetero atom,

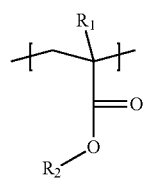

[Formula 2]

wherein the $R_1$ is hydrogen or an alkyl group and the $R_2$ is an alkyl group that is not substituted with a halogen atom.

2. The block copolymer according to claim 1, wherein the $X_2$ is the single bond or the oxygen atom.

3. The block copolymer according to claim 1, wherein the linear chain comprises 9 to 20 chain-forming atoms.

4. The block copolymer according to claim 1, wherein the chain-forming atom is a carbon, an oxygen, a nitrogen or a sulfur.

5. The block copolymer according to claim 1, wherein the chain-forming atom is a carbon or an oxygen.

6. The block copolymer according to claim 1, wherein the hetero atom is an oxygen atom.

7. The block copolymer according to claim 1, wherein the linear chain is alkoxy group or alkoxyalkyl group.

8. The block copolymer according to claim 1, wherein the $R_1$ of the Formula 2 is an alkyl group having 1 to 4 carbon atom(s).

9. The block copolymer according to claim 1, wherein the $R_2$ of the Formula 2 is an alkyl group having 1 to 4 carbon atom(s).

10. A polymer layer comprising a self assembled product of the block copolymer of claim 1.

11. A method for forming a polymer layer, comprising forming the polymer layer comprising a self assembled product of the block copolymer of claim 1.

12. A pattern-forming method comprising selectively removing the first block or a second block different from the first block of the block copolymer from a laminate comprising a substrate and a polymer layer that is formed on the substrate and that comprises a self-assembled product of the block copolymer of claim 1.

* * * * *